United States Patent [19]

Caspari et al.

[11] Patent Number: 5,304,181
[45] Date of Patent: Apr. 19, 1994

[54] METHODS AND APPARATUS FOR ARTHROSCOPIC PROSTHETIC KNEE REPLACEMENT

[76] Inventors: Richard B. Caspari, 2192 Sheppard Town Rd., Maidens, Va. 23102; Jeffrey G. Roberts, 3688 Montclair Dr., Palm Harbor, Fla. 34684; James T. Treace, 2701 Bluffs Dr., Largo, Fla. 34640

[21] Appl. No.: 773,213

[22] Filed: Oct. 9, 1991

Related U.S. Application Data

[62] Division of Ser. No. 462,529, Jan. 8, 1990.

[51] Int. Cl.⁵ .............................................. A61B 17/32
[52] U.S. Cl. ........................................ 606/80; 606/88; 606/167; 606/170; 606/180; 604/35; 407/54
[58] Field of Search ................... 606/80, 81, 87, 88, 606/96, 167, 170, 180, 183, 1, 79, 86, 89-91, 97-98, 168, 169, 171; 604/22, 27, 35; 408/56-59, 67, 88, 99, 110, 203.5, 237; 407/53, 54

[56] References Cited

U.S. PATENT DOCUMENTS

| | | |
|---|---|---|
| 1,869,514 | 8/1932 | Seitz .................................. 408/237 |
| 3,037,264 | 6/1962 | Mossberg ............................. 407/53 |
| 3,229,427 | 1/1966 | Goodhew ............................ 408/57 |
| 3,456,316 | 7/1969 | Dawson .............................. 407/53 |
| 3,548,476 | 12/1970 | Cave et al. .......................... 407/54 |
| 3,694,099 | 9/1972 | Nicholas ............................. 408/58 |
| 4,349,018 | 9/1982 | Chambers . |
| 4,421,112 | 12/1983 | Mains et al. . |
| 4,457,307 | 7/1984 | Stillwell .............................. 606/88 |
| 4,467,801 | 8/1984 | Whiteside . |
| 4,487,203 | 12/1984 | Androphy . |
| 4,502,483 | 3/1985 | Lacey . |
| 4,524,766 | 6/1985 | Petersen . |
| 4,567,885 | 2/1986 | Androphy . |
| 4,567,886 | 2/1986 | Peterson . |
| 4,574,794 | 3/1986 | Cooke et al. ........................ 606/88 |
| 4,646,729 | 3/1987 | Kenna et al. . |
| 4,653,488 | 3/1987 | Kenna . |
| 4,677,973 | 7/1987 | Slocum . |
| 4,703,751 | 11/1987 | Pohl . |
| 4,718,413 | 1/1988 | Johnson . |
| 4,719,908 | 1/1988 | Averill et al. . |
| 4,721,104 | 1/1988 | Kaufman et al. . |
| 4,722,330 | 2/1988 | Russell et al. . |
| 4,736,737 | 4/1988 | Fargie et al. . |
| 4,738,253 | 4/1988 | Buechell et al. . |
| 4,738,254 | 4/1988 | Buechell et al. . |
| 4,757,810 | 7/1988 | Reese . |
| 4,759,350 | 7/1988 | Dunn et al. . |
| 4,773,407 | 9/1988 | Petersen . |
| 4,787,383 | 11/1988 | Kenna . |
| 4,791,919 | 12/1988 | Elloy et al. . |
| 4,822,362 | 4/1989 | Walker et al. . |
| 4,825,857 | 5/1989 | Kenna . |
| 4,862,881 | 9/1989 | Shea, Jr. . |
| 4,893,968 | 1/1990 | Levy .................................... 407/53 |
| 4,921,375 | 5/1990 | Famulari .............................. 408/67 |
| 4,936,313 | 6/1990 | Burkhardt et al. ................. 606/180 |
| 5,047,032 | 9/1991 | Jellicoe ................................ 606/87 |

FOREIGN PATENT DOCUMENTS 0333651  9/1989  European Pat. Off. ......... 408/203.5

OTHER PUBLICATIONS

The S-ROM TM Tri-Version TM Femoral Stem System.
The Freeman Total Hip System.

Primary Examiner—Stephen C. Pellegrino
Assistant Examiner—Glenn Dawson

[57] ABSTRACT

Methods and apparatus for prosthetic knee replacement permit preparation of tibial plateau and femoral condyle surfaces and implant of tibial and femoral protheses components with the use of arthroscopic surgical techniques. The bone surfaces are resected by moving a rotating milling cutter longitudinally across the bone surface and moving the rotating milling cutter substantially laterally across the bone. Cement is supplied between the prostheses and the bone surfaces after positioning of the prostheses on the bone, and cement bonding is enhanced by applying suction to the bone to draw the cement into the bone. The apparatus for resecting the bone surfaces includes a rotating milling cutter having a body with cutting edges and holes extending through the body communicating with the interior of the body. Suction is applied to the end of the body to draw out tissue fragments through the holes and out of the body.

14 Claims, 12 Drawing Sheets

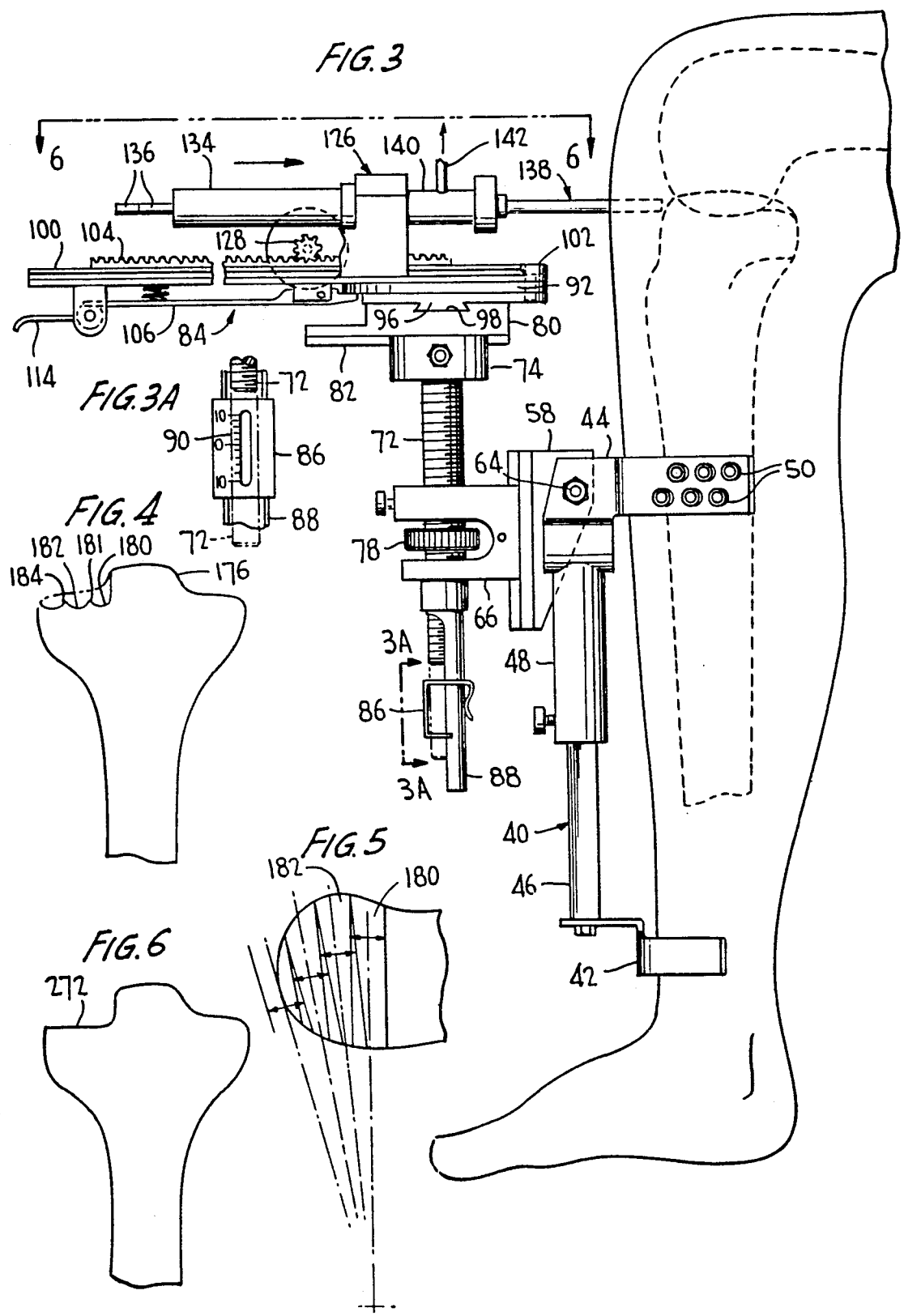

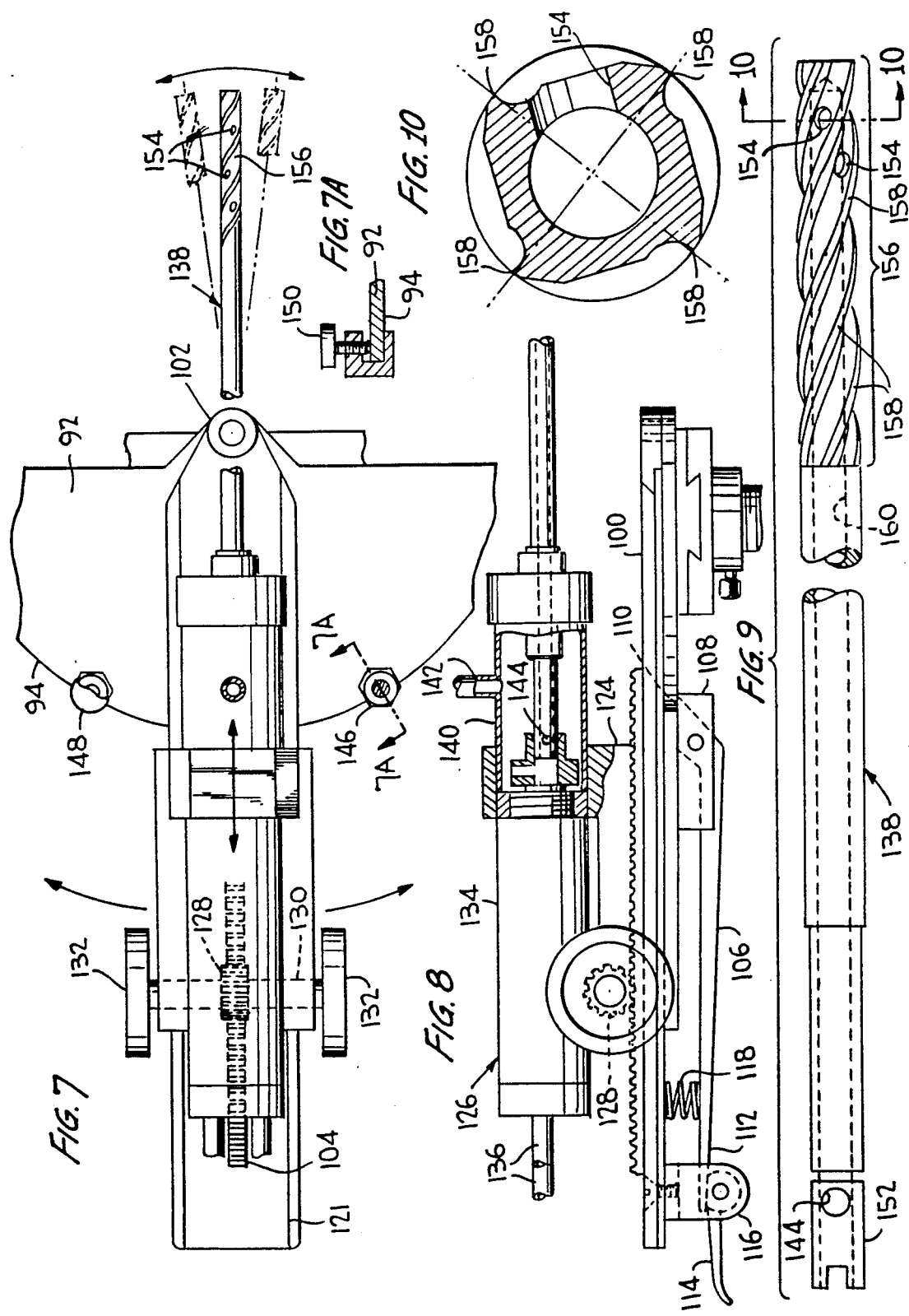

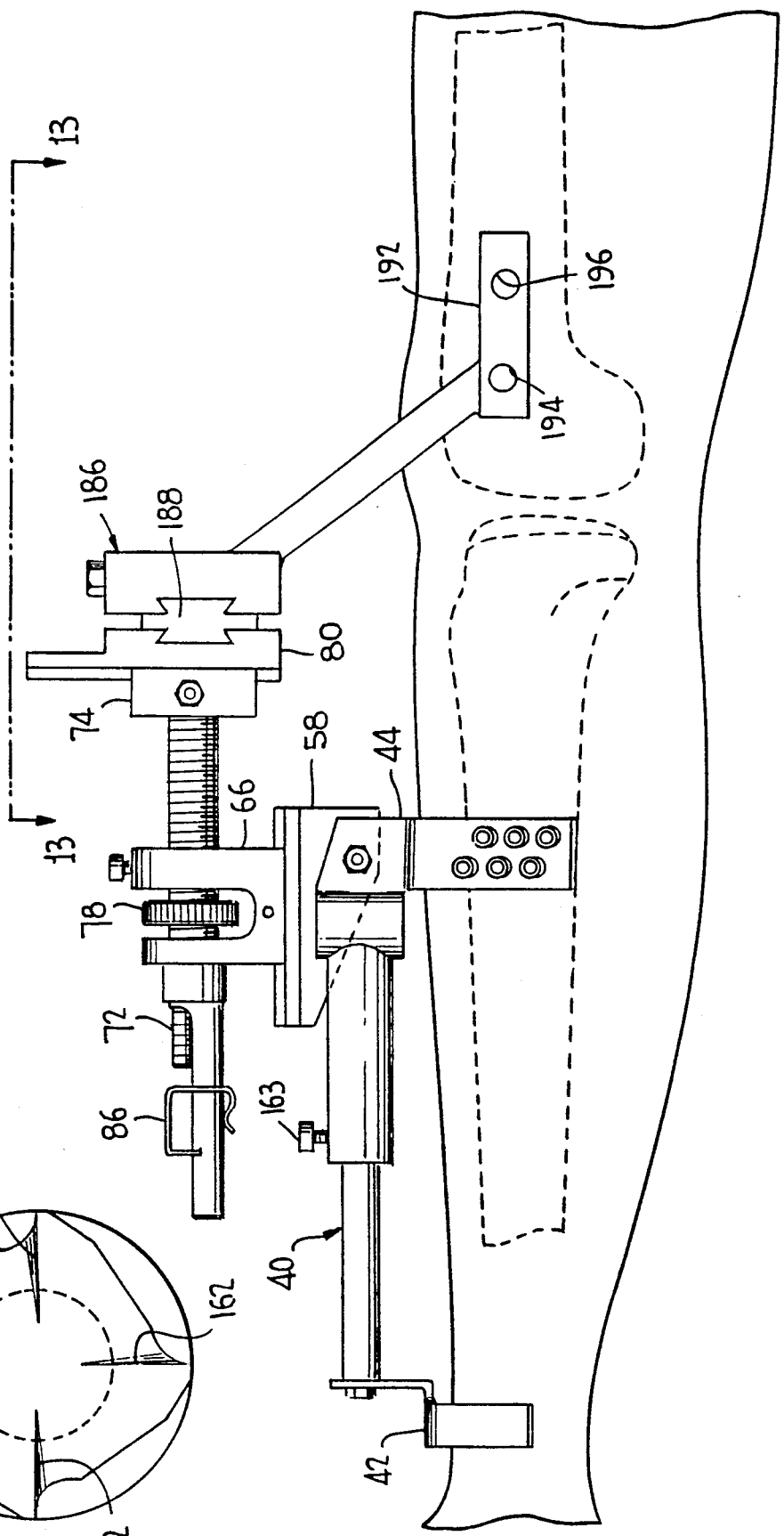
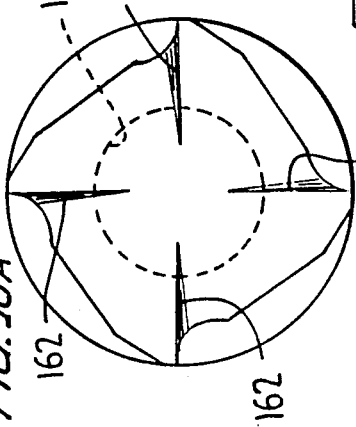
FIG. 10A
FIG. 11

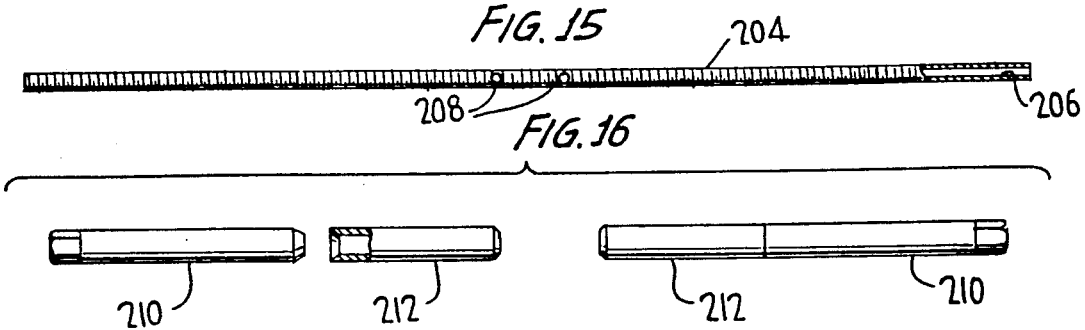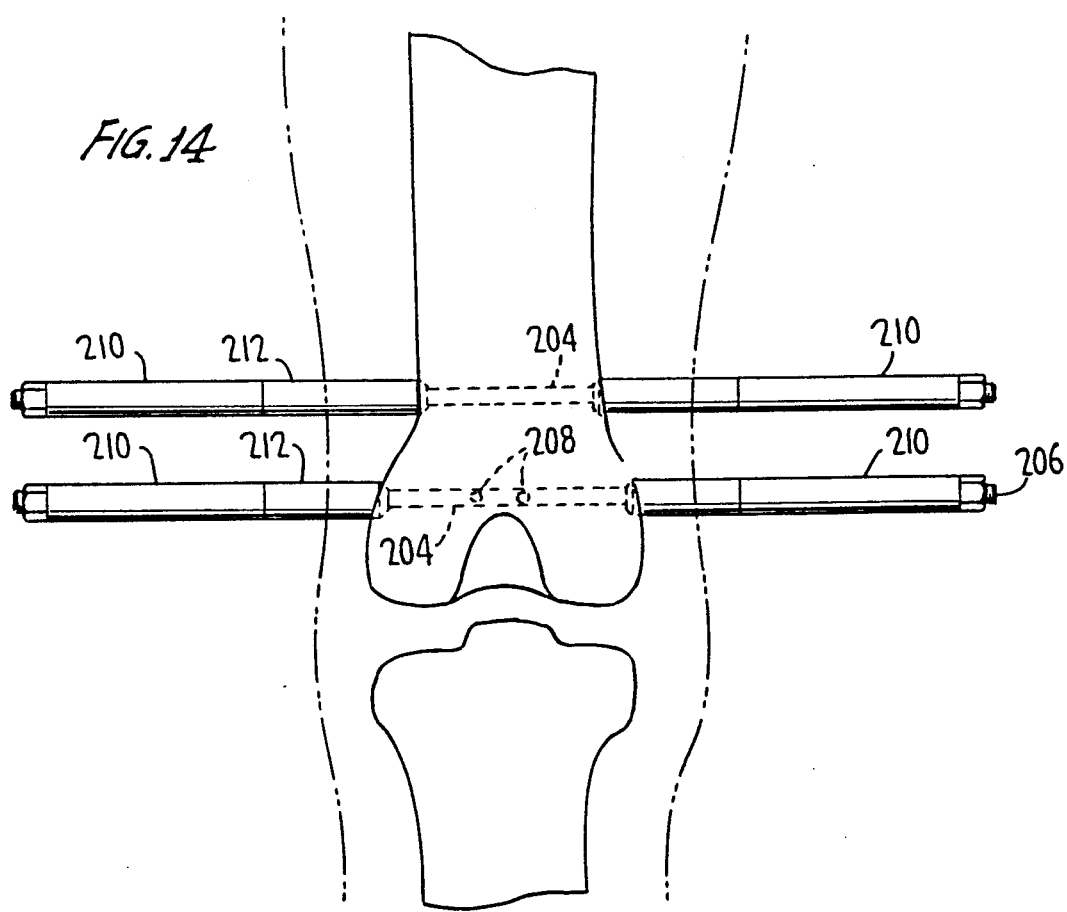

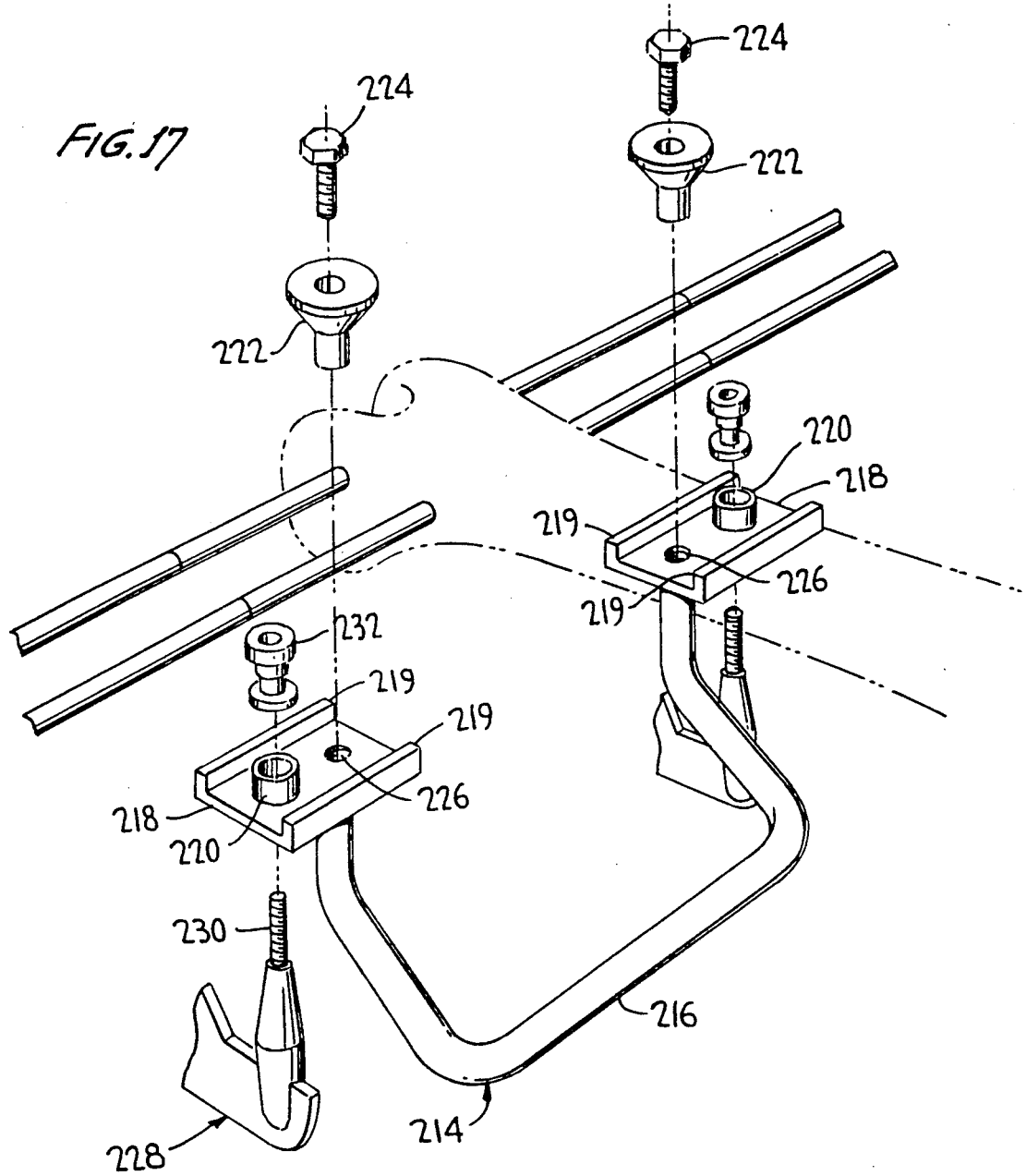

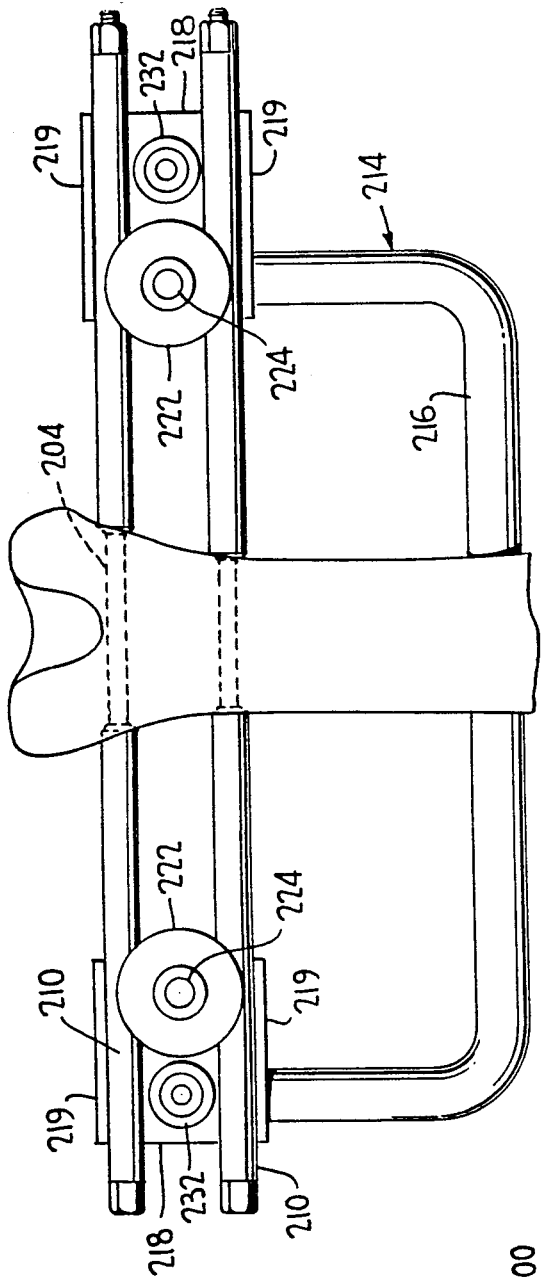
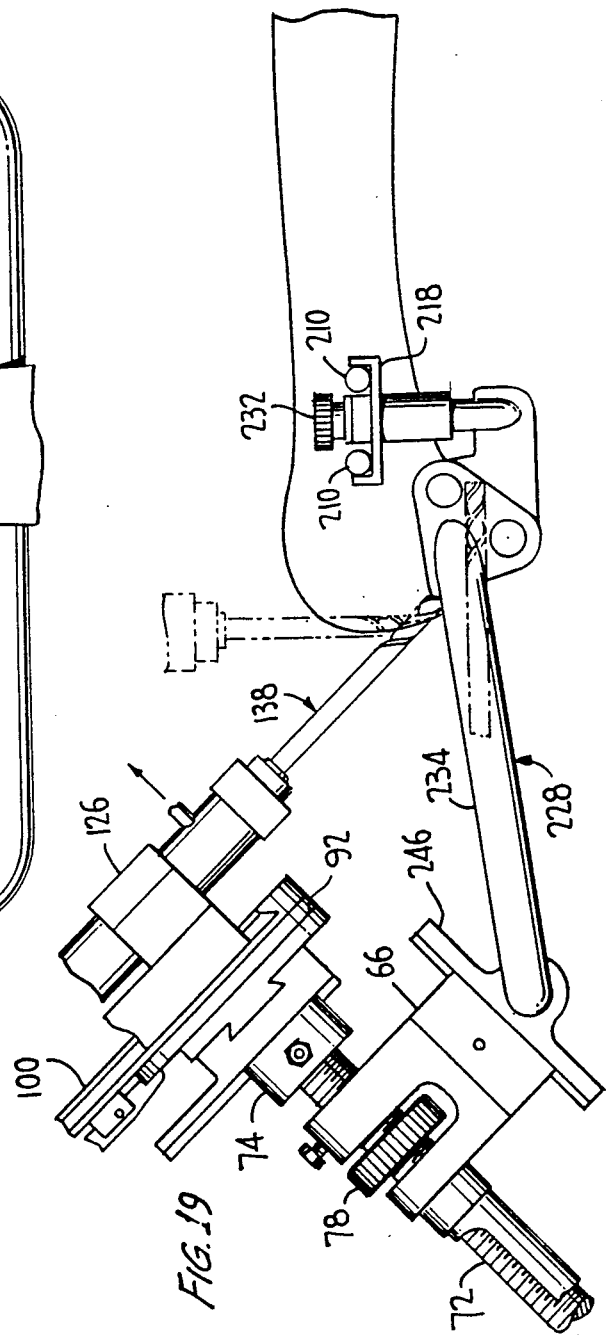

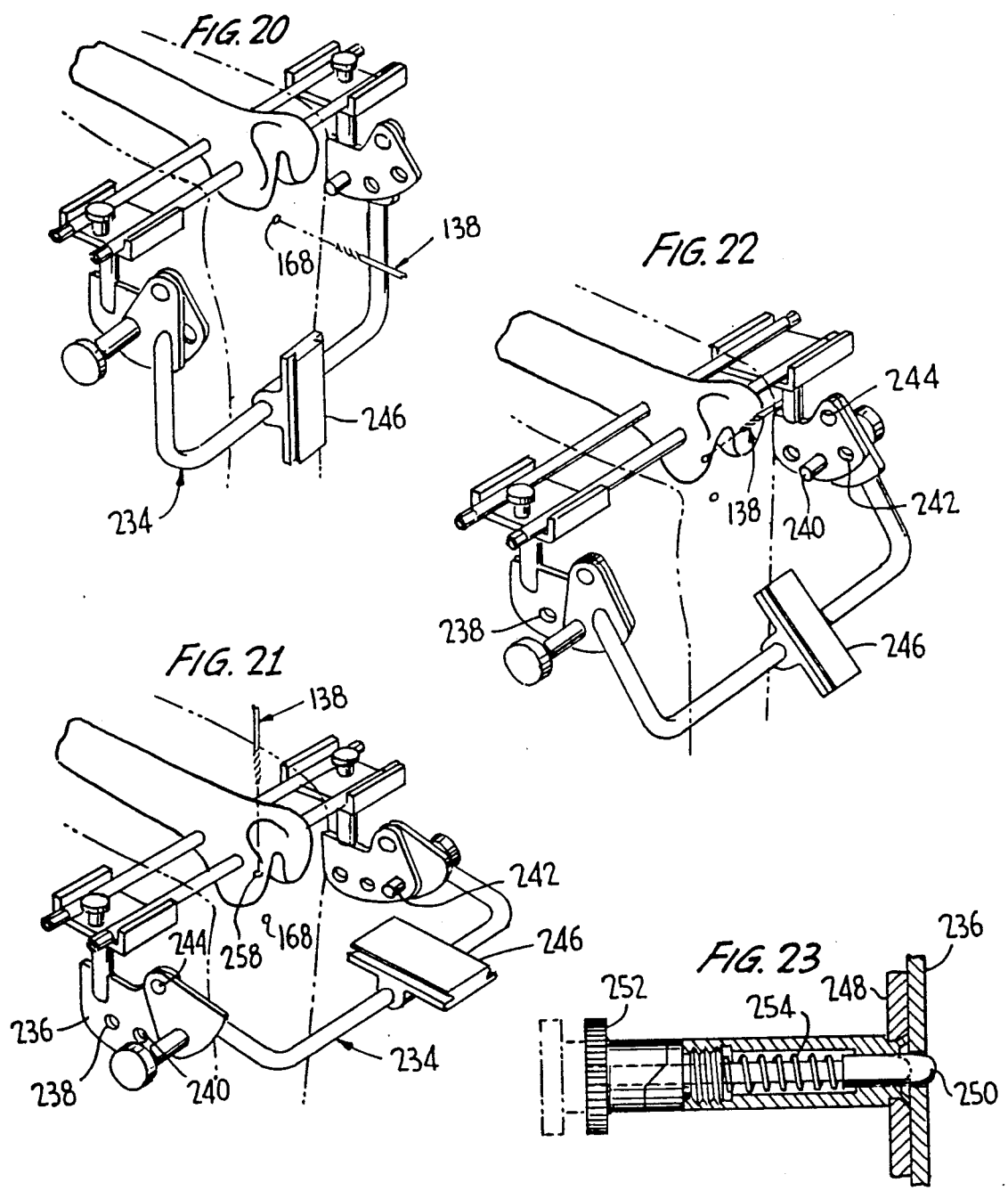

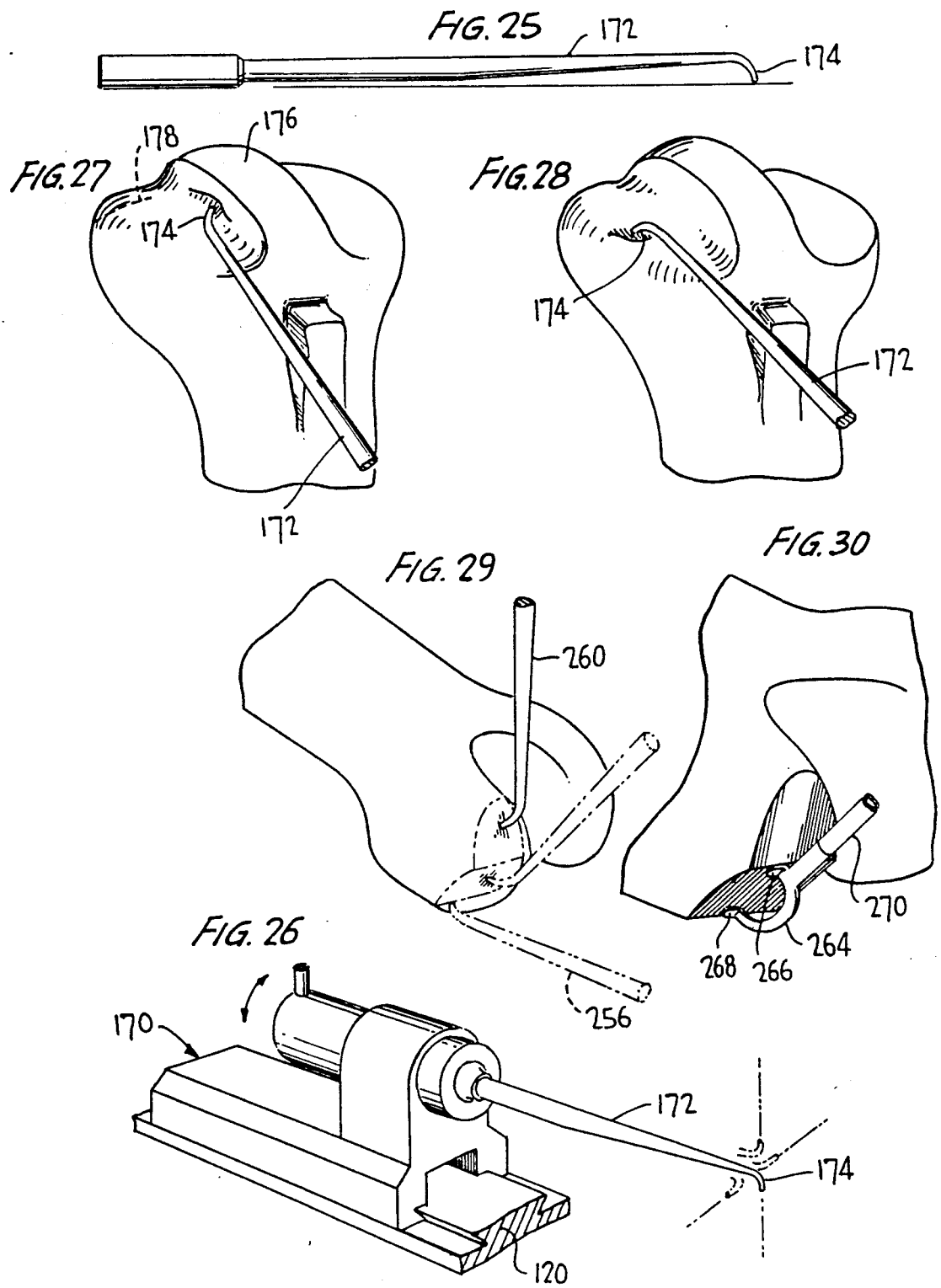

METHODS AND APPARATUS FOR ARTHROSCOPIC PROSTHETIC KNEE REPLACEMENT

This is a divisional application of application Ser. No. 07/462,529 filed Jan. 8, 1990.

BACKGROUND OF THE INVENTION

1. Field of the Invention:

The present invention pertains to resection of bones for receiving prosthetic components of particular use in knee replacement procedures and, more specifically, to methods and apparatus for arthroscopic knee replacement.

2. Discussion of the Prior Art:

Prosthetic replacement of the knee is a procedure of substantial importance to recreate the knee joint with a pain-free functional arc of motion and antero-posterior and varus-valgus stability. The knee is, basically, formed of medial and lateral tibial plateaus, medial and lateral femoral condyles and menisci between the tibial plateaus and the femoral condyles along with the patella which covers the anterior surface of the knee, and prosthetic replacement of the knee as described herein relates to the tibial plateaus, the femoral condyles and the menisci. Various types of prostheses are presently available, as described in detail in *Replacement of the Knee*, Laskin, Denham and Apley, Springer-Verlag Berlin Heidelberg, 1984, and are commonly grouped as partial or unicompartmental replacements of the medial or lateral portion of the tibio-femoral joint, surface replacements to prevent contact between worn surfaces and jack the joint surfaces apart, linked joints and fixed hinge joints. The type of prosthesis employed must be matched to the needs of the patient. By selecting the proper prothesis, antero-posterior and varus-valgus stability can be achieved by prosthetic replacement coupled with bone surfacing or resection. In the past, prosthetic replacement has been a last resort in treatment for knee problems due to the facts that prior art protheses and surgical procedures have not led to reliable, close to natural, results and the open surgery required results in great trauma and substantial recovery time. Much effort has been expended in attempts to improve the accuracy with which articular joint surfaces can be positioned with leg alignment; however, procedures and apparatus available at this time do not provide the required accuracy to restore normal leg alignment and prevent early failure of the prothesis.

Open surgery required for prior art prosthetic replacements typically necessitates a long incision, on the order of ten inches, along the anterior midline of the knee from above the patella to below the tibial tubercle followed by a deep dissection around the medial border of the patella and along the patellar ligament to the tibial tubercle with detachment of the medial third of the quadriceps attachment from the upper border of the patella. The tendinous margin is then pulled downwards and medially while the patella is pulled downwards and laterally. The quadriceps tendon is then split, and the patella is displaced laterally and everted. While the above is a simplified explanation of open knee surgery, it serves to explain the substantial trauma and recovery time associated therewith. Arthroscopic surgery has been used for many surgical procedures on the knee to avoid open surgery with great success; however, the obstacles presented by articular bone surface resecting or shaping to receive an implant coupled with the need for precise positioning and alignment of the prostheses has been insurmountable with arthroscopic procedures prior to the present invention. Not only is there a great need for an arthroscopic prosthetic knee replacement procedure but there is also a great need for improvement in the accuracy of prosthesis placement to restore normal leg alignment.

SUMMARY OF THE INVENTION

Accordingly, it is a primary object of the present invention to overcome the above mentioned disadvantages associated with prior art prosthetic knee replacement surgical procedures with an arthroscopic prosthetic knee replacement.

Another object of the present invention is to accurately resect tibial plateau and femoral condyle planar surfaces relative to each other such that the tibial plateau and femoral condyle surfaces are constrained to be disposed in planes perpendicular to a substantially vertical reference plane.

A further object of the present invention is to cement a prosthesis to a tissue surface after the prosthesis is accurately placed on the tissue surface.

An additional object of the present invention is to perform a least invasive prosthetic knee replacement with the use of arthroscopy and requiring only arthroscopic size portals.

The present invention has another object in the performing of all procedures for a prosthetic knee replacement, including surface preparation, fitting and implanting, arthroscopically through small portals enlarged only for insertion of the final components.

Yet an additional object of the present invention is to arthroscopically resect tibial plateau an femoral condyle surfaces using existing surface anatomy as a reference point.

A further object of the present invention is to improve the mechanical bond created by cement between a prosthesis and a bone surface by applying suction to the bone to draw the cement into the bone.

Some of the advantages of the present invention over prior art prosthetic knee replacements are that, by using arthroscopic surgical techniques and small portals in place of the long incisions required for open knee procedures, trauma and recovery time are substantially reduced, alignment of the tibial and femoral prosthesis components is assured by fixing the femoral cutting jig with reference to the tibial cutting jig and, therefore, resecting the femoral condyle with reference to the resected tibial plateau, the knee is restored to a normal, healthy condition by resecting the tibial plateau and the tibial condyle using the existing surface anatomy as a reference point, and prostheses are cemented after accurate positioning of the prostheses on the bone.

Generally, the present invention contemplates the use of a milling cutter to prepare a bone surface to receive a prosthesis such that bone surfaces can be resected through small portals allowing prosthesis implantation using arthroscopic surgical techniques and, more particularly, allowing arthroscopic, unicompartmental, prosthetic total knee replacement. Tibial and femoral prosthesis components are bonded to the bone surfaces by injecting cement after the components are accurately positioned on the bone, the cement being injected through the components to be received in chambers defined by recesses in the fixation surfaces of the components and the cement bond being enhanced by applying suction to the bone to draw the cement into the bone.

Other objects and advantages of the present invention will become apparent from the following description of the preferred embodiment taken in conjunction with the accompanying drawings.

BRIEF DESCRIPTION OF THE DRAWINGS

FIG. 3 is a side view of the apparatus of FIG. 2 in position for resecting the tibial plateau.

FIG. 3a is a view taken along lines 3a—3a of FIG. 3 showing a depth of gauge scale.

FIG. 4 is a front view of the tibial plateau during the resecting thereof.

FIG. 5 is a top view of the tibial plateau after longitudinal cuts are made therein.

FIG. 6 is a side view of the tibial plateau after resecting to produce a planar tibial plateau surface.

FIG. 7 is a plan view of the milling cutter module mounted on a support platform.

FIG. 7a is a section taken along lines 7A—7A of FIG. 7 showing a stop for limiting pivotal movement of the milling cutter.

FIG. 8 is a side view, partly in section, of the milling cutter module on a slide member of the platform.

FIG. 9 is a broken plan view of the milling cutter according to the present invention.

FIG. 10 is a section taken along lines 10—10 of FIG. 9.

FIG. 10a is a distal end view of the milling cutter of FIG. 9.

FIG. 11 is a side view of the cutter platform with an alignment bridge mounted thereon for drilling holes in the femur.

FIG. 14 is a top view showing rods passing through the holes drilled in the femur for attachment of a femoral jig.

FIG. 15 is a broken side view partly in section of a rod for passing through the femur.

FIG. 16 is an exploded broken view, partly in section, of sleeves received on the rods.

FIG. 17 is an exploded perspective view of a femoral support base.

FIG. 18 is a top plan view of the femoral support base.

FIG. 19 is a broken side view of the femoral jig with the cutter platform and the cutter module mounted thereon.

FIGS. 20, 21 and 22 are perspective views showing resecting of a femoral condyle to produce planar posterior, distal and chamfer surfaces, respectively.

FIG. 23 is a broken section of a holding detent for the tibial jig.

FIG. 25 is a side view of a stylus for use in resecting the tibial plateau and the femoral condyle.

FIG. 26 is a perspective view of a module for the stylus mounted on the platform slide member.

FIGS. 27, 28 and 29 are perspective views showing use of the stylus for positioning the cutter platform for resecting the tibial plateau and the femoral condyle.

FIG. 30 is a broken perspective view showing use of a gauge for selecting the size of a femoral prosthesis component.

DESCRIPTION OF THE PREFERRED EMBODIMENT

The apparatus and method for prosthetic knee replacement in accordance with the present invention requires only small portals to perform all bone and tissue preparation procedures as well as implanting the prosthetic tibial and femoral components and cementing the components in place. Accordingly, prosthetic knee replacement in accordance with the present invention can be performed with the use of arthroscopic surgical procedures. By "portal" is meant a puncture or stab wound of the type made by a plunge cut with a scalpel or trocar and of the type commonly used in conventional arthoscopic procedures, the size of the portal being just large enough to allow insertion of instruments.

Figure 1:
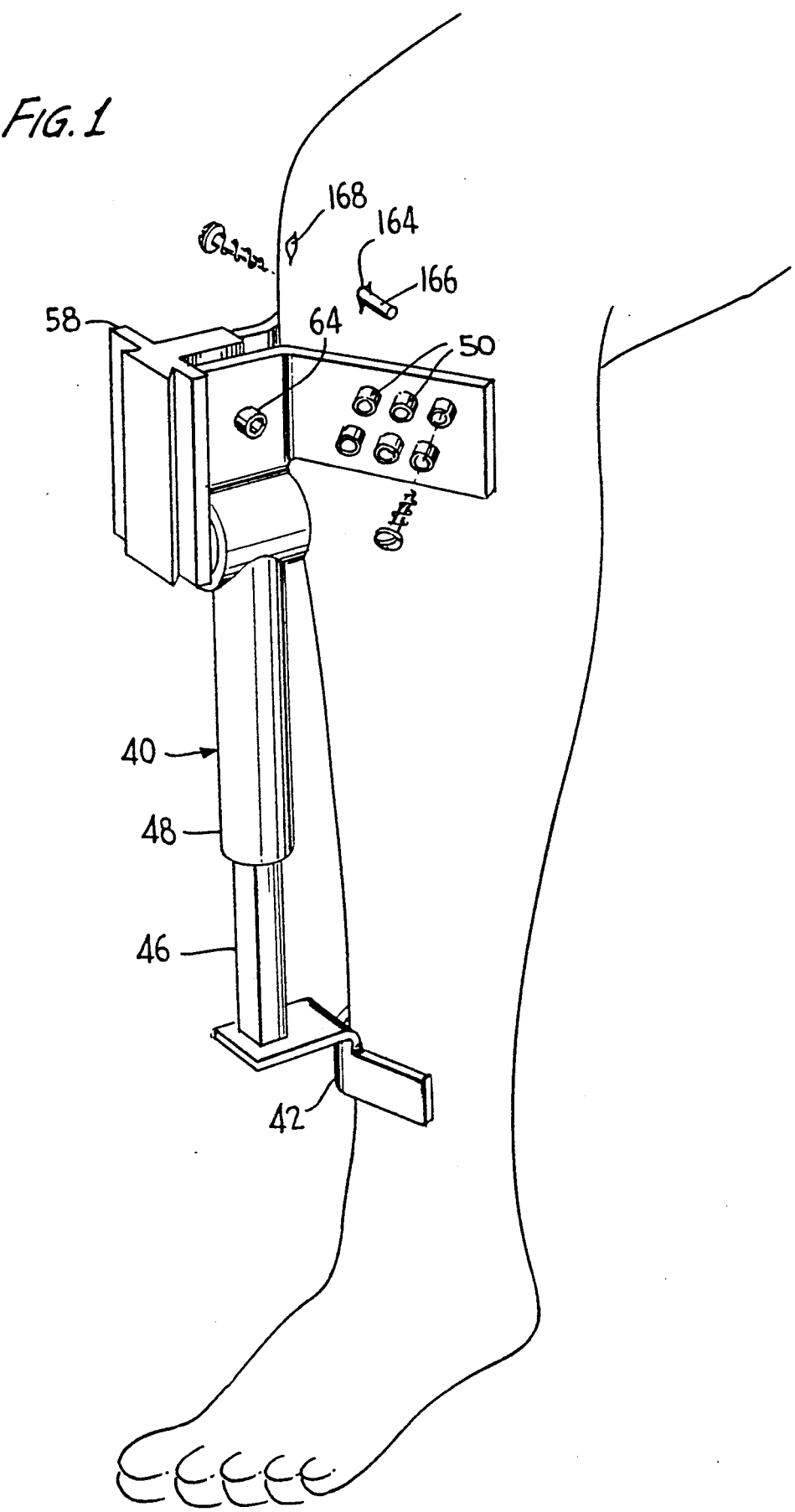
FIG. 1 is a perspective view of a tibial jig mounted to the tibia in accordance with the present invention.
Figure 2:
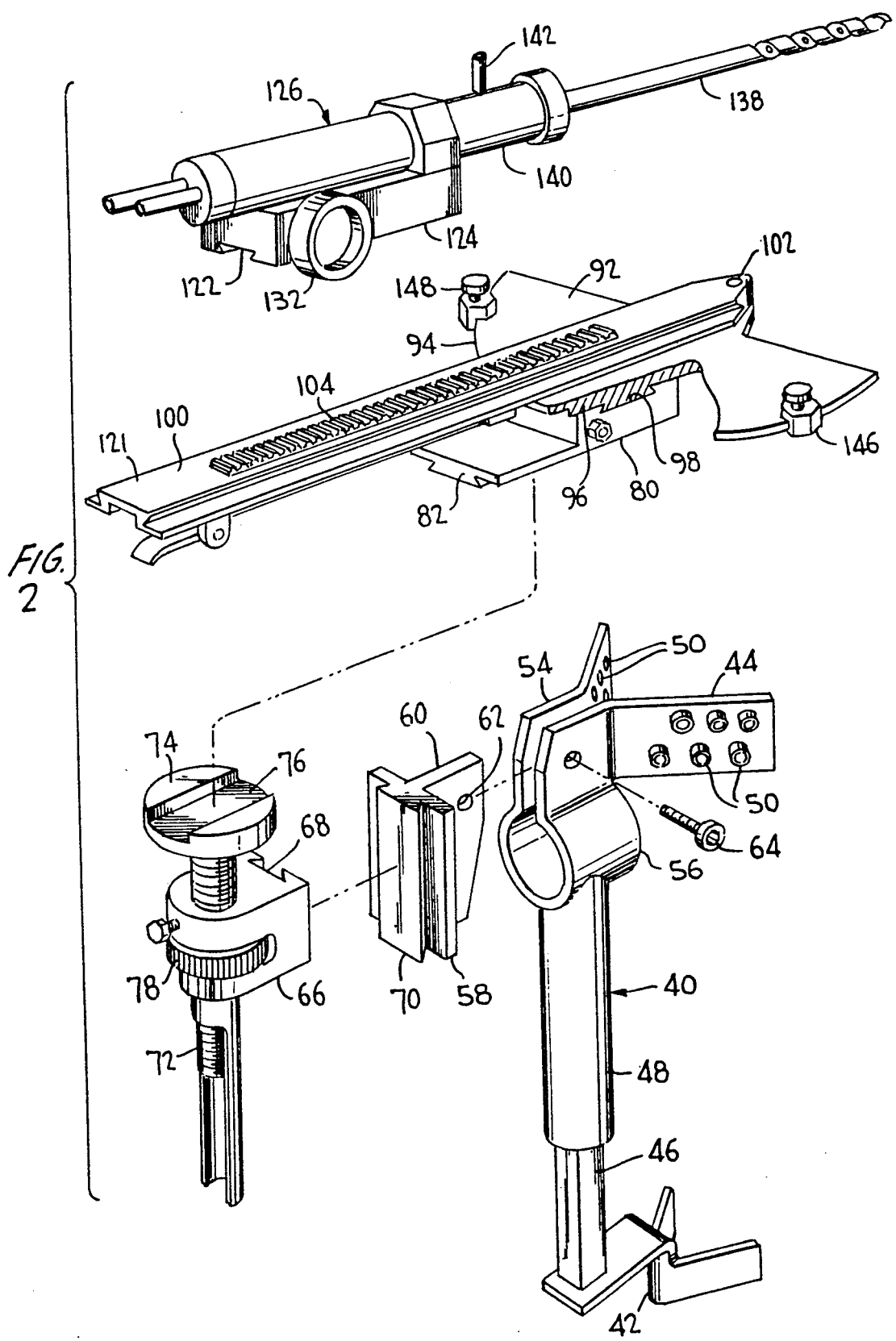
FIG. 2 is an exploded view of the tibial jig, a support assembly and a milling cutter module in accordance with the present invention.

A tibial jig 40 in accordance with the present invention is illustrated in FIG. 1 and includes a lower V-block 42 adapted to rest just above the malleoli at the ankle and an upper V-block 44 adapted to be secured to the tibia just below the tibial tubercle. Lower V-block 42 is connected to a rod 46 telescopingly received within a tube 48 connected to upper V-block 44 which is formed of a pair of angled members having a plurality of holes 50 therein to receive screws 52 extending therethrough and into the tibia to securely mount the tibial jig thereon. As best shown in FIG. 2, tube 48 has spaced arms 54 and 56 terminating at the angled members of upper V-block 44, and an angular adjustment member 58 has a tongue 60 disposed between members 54 and 56 with a hole 62 therein for receiving an adjustment screw 64 extending through corresponding holes in members 54 and 56. In this manner, the angular adjustment member 58 can be pivoted about screw 64 to a desired position and the screw tightened to hold the angular adjustment member in place. A longitudinal adjustment block 66 has a dovetail slot 68 therein to receive a dovetail 70 on member 58, and a longitudinal adjustment screw 72 is held in a non-rotating manner in block 66 and carries a head 74 having a dovetail slot 76 therein. Block 66 has spaced arms between which is mounted a thumbwheel 76 threadedly engaging adjustment screw 72 such that rotation of thumbwheel 76 causes longitudinal axial movement of the screw and the head. A block 80 has a dovetail 82 received in slot 76 and mounts a cutter platform generally indicated at 84. As shown in FIGS. 3 and 3a, a longitudinal or depth of cut gauge 86 is mounted on an extension 88 of block 66 and carries indicia 90 allowing registration with an index mark on screw 72 to indicate the depth of a cut being made, as will be explained in more detail hereinafter. The gauge has a zero center mark with indicia extending in either direction therefrom in millimeter graduations.

The platform 84 includes a semi-circular plate 92 having a curved peripheral edge 94 and a dovetail 96 slidably received in a dovetail slot 98 in block 80 to permit movement of the platform in a lateral direction perpendicular to the longitudinal movement of screw 72. A linear slide member 100 has a distal end 102 pivotally mounted centrally on plate 92 and carries a toothed rack 104 longitudinally thereon. The slide member 100 extends substantially beyond the peripheral edge 94 of plate 92 and carries on its back side a clamp assembly including a lever 106 pivotally mounted on ears 108 secured to the slide member, the lever 106 having a clamping end 110 and an operating end 112 as best shown in FIG. 8. A trigger like member 114 is pivotally mounted on a lug 116 extending from the slide member and has a flat portion engaging the operating end 112 of lever 106 which is biased against the trigger by means of a compression spring 118. Accordingly, when trigger 114 is moved toward the slide member (rotated clockwise looking at FIG. 8) the operating end 112 of lever 106 is moved toward the slide member causing the clamping end 110 to move away from the peripheral edge 94 of plate 92 thereby allowing pivotal movement of the slide member relative to the plate. When the trigger 114 is released, the spring 118 returns the clamping end 110 to engagement with the plate to hold the slide member in the selected pivotal position.

The slide member has an elongated dovetail 121 received in a slot 122 in a housing 124 of a cutter module generally indicated at 126. A pinion 128 having teeth for engaging rack 104 is mounted on an axle journaled through housing 124 to terminate at handwheels 132 on either side of the housing. A pneumatic motor 134 has a proximal end receiving drive and exhaust conduits 136 and a distal end engaging the shaft of a milling cutter 138 as best shown in FIG. 8. The motor is driven by pressurized fluid, such as nitrogen or air; and, when the drive fluid is provided at 100 psi, the motor speed and torque are 4000 rpm and 50 oz-inch, respectively. A chamber 140 is formed around the drive coupling and has a port 142 for connection to a source of suction, the proximal end of the milling cutter 138 having a hole 144 therein for communicating with the chamber and the milling cutter 138 being rotatably supported at the distal end of the chamber by suitable bearing and journal structure. Stops 146 and 148 are movably secured to the peripheral edge 94 of plate 92 on opposite sides of slide member 100; and, as shown in FIG. 7a, are formed of set screws 150 for engaging the plate 92.

The milling cutter 138, as best shown in FIGS. 9, 10 and 10a, includes a shaft having a proximal end 152 for engaging a locking collet assembly in chamber 140 to be driven by the pneumatic motor, the shaft being hollow to establish communication between hole 144 in the proximal end thereof and holes 154 disposed in the distal portion thereof. The distal portion of the milling cutter includes a body 156 having a plurality of helical cutting edges 158 extending therealong, and at least one hole 154 is disposed between each pair of body cutting edges 158. As shown in FIG. 10, four equally spaced cutting edges are disposed on the fluted body 156, and holes 154 communicate with a passage 160 formed by the hollow shaft of the milling cutter. Cutting edges 162 are disposed at the distal end of the milling cutter in a plane extending transverse to the longitudinal axis of the milling cutter, and each of the body cutting edges 158 extends from one of the distal end cutting edges 162. The milling cutter preferably has a diameter of 7 mm and the body cutting edges preferably have substantially radial leading edges.

The operation of the apparatus described above to resect a tibial plateau for unicompartmental prosthetic knee replacement utilizing arthroscopic surgical techniques will be described with reference to FIGS. 1 and 3. As previously described, tibial jig 40 is secured to the tibia by screws 52 extending through V-block 44 and into the tibia with the upper and lower V-blocks disposed just below the tibial tubercle and just above the malleoli at the ankle, respectively, with a set screw 163 provided to maintain the position of telescoping members 46 and 48. A portal 164 is formed in the knee for insertion of an arthroscope 166 for viewing of the knee and the surgical procedure, while a portal 168 is formed in the tissue adjacent the tibial plateau, FIG. 1 illustrating the portal 168 for use in resecting the medial tibial plateau of the left leg. With the tibial jig 40 secured in alignment with the tibia, the apparatus is assembled as illustrated in FIG. 3 with the exception that the cutter module is not mounted on the slide member 100 but rather a stylus module 170, as illustrated in FIG. 26, is mounted thereon. The stylus module 170 includes a housing having a dovetail slot for receiving the dovetail 120 of the slide member and mounts a stylus 172 having four equally spaced positions controlled by detents, not shown, within the housing. The stylus has a curved radially extending tip 174 that can be positioned via the detents to extend up, down or to either side. The radial extension of the stylus 174 is preferably equal to the radius of the milling cutter, e.g., 3.5 mm, and the housing of the stylus module positions the stylus at the same position at which the milling cutter is positioned when the cutter module is received on the slide member. With the stylus tip turned down, the posterior and anterior edges of the tibial plateau are contacted with the stylus, and angular adjustment block 58 is pivoted about screw 64 to align the platform with the natural tilt of the tibial plateau as sensed by the stylus, the natural tilt being normally between 3° and 10° posteriorly. Once the natural tilt is established, the stylus is rotated 90° such that the tip 174 is turned to the right, and the tip of the stylus is moved by sliding the plate 92 in block 80 until the tip of the stylus contacts the tibial eminence 176 as illustrated in FIG. 27. Once the tibial eminence has been located, a screw, not shown, is tightened to secure the lateral position of the platform. The slide member 100 is centrally positioned on the plate 92 during this procedure, and the stop 148 is moved to abut the slide member 100 to prevent pivotal movement of the slide member and the milling cutter mill clockwise looking at FIG. 7. With the tip 174 of the stylus turned down, the lowest point of contact of the tip on the tibial plateau is located; and, with the stylus at this contact point, thumbwheel 78 is locked in place to control the position of the resection to be performed, it being noted that, due to the dimensional relationship between the cutter module and the stylus module, the milling cutter will be aligned with the lowest point on the tibial plateau. As shown in dashed lines in FIG. 27, prior to the alignment steps, the anterior portion of the meniscus or cartilage has been removed by normal arthroscopic techniques leaving a posterior segment indicated at 178 such that during the resection procedure, the posterior portion of the meniscus provides a cushion to provide the surgeon with an indication of the location of the posterior edge of the tibial plateau.

To resect the tibial plateau, the stylus module is removed and the cutter module is placed thereon as illustrated in FIG. 3; and, since angular, lateral and longitudinal adjustments have already been made and set in place, only linear and pivotal movements of the milling cutter can be made and such movements can be made only in a single plane. With reference to FIGS. 4 and 5, it can be seen that initial forward movement of the milling cutter produces a longitudinal plunge cut along the tibial eminence 176 to produce a trough across the tibial plateau as indicated at 180, it being noted that the milling cutter cuts on its distal end as well as along the fluted body thereof. After the first longitudinal cut has been made, the trigger 114 is released allowing pivotal movement of the slide member slightly; and, after the trigger is released to clamp the slide member in position, a second longitudinal cut is made by linear movement of the milling cutter as indicated at 182. This procedure is repeated until the surface of the tibial plateau is covered with troughs having ridges 184 therebetween. The trigger 114 is now depressed to release the slide member; and, with the milling cutter disposed over the tibial plateau, the milling cutter is pivoted back and forth to sweep the milling cutter over the tibial plateau removing the ridges, the sweeping movement being substantially transverse to the longitudinal movements of the milling cutter to form the troughs. During the resecting procedure, suction is applied to port 142 such that bone chips are evacuated via holes 154 and passage 160 through the hollow milling cutter. The suction also serves to cool the surgical site and prevent cavitation.

Figure 12:
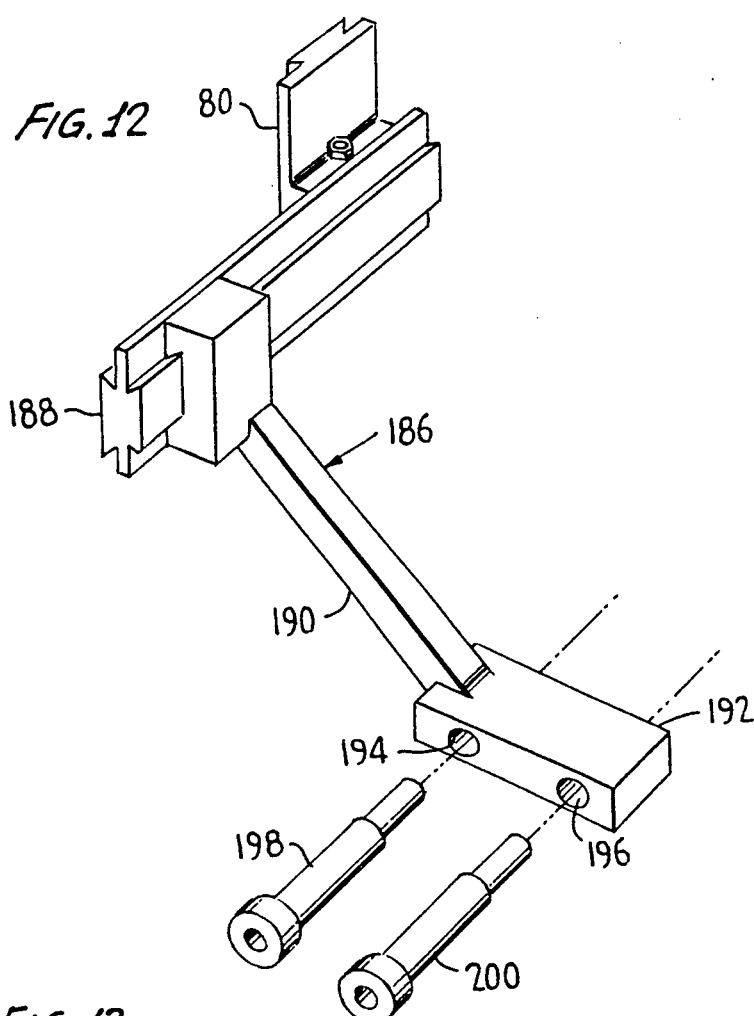
FIG. 12 is a perspective view of the alignment bridge.
Figure 13:
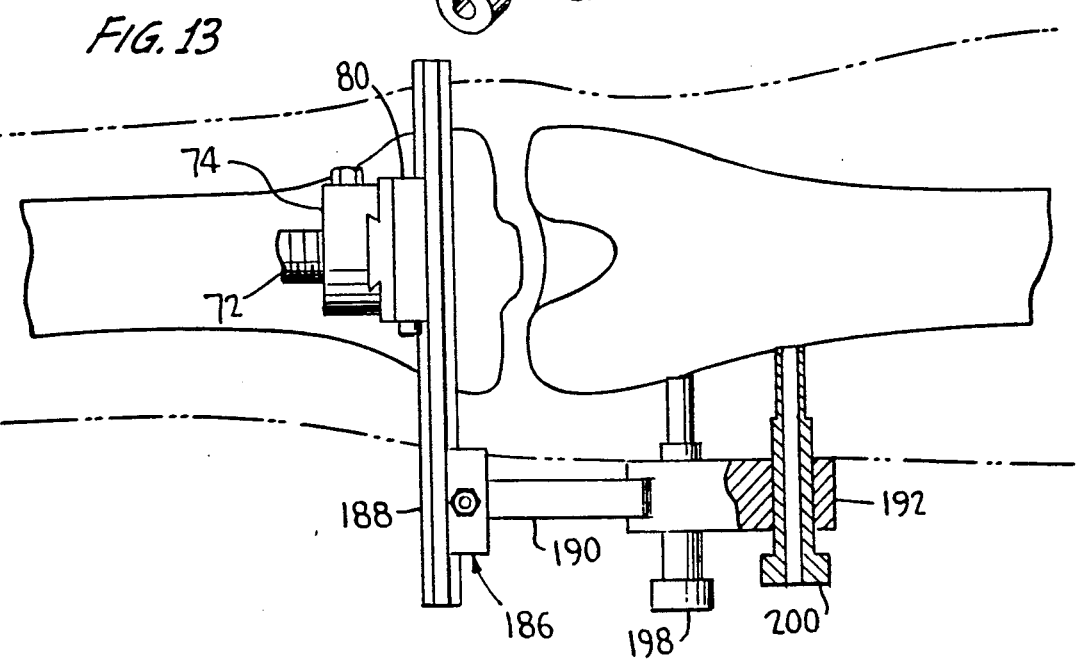
FIG. 13 is a top view taken along line 13—13 of FIG. 11.

Once the tibial plateau has been resected, the cutter module is removed from the platform, and the platform is removed from block 80. An alignment bridge 186, as illustrated in FIG. 12, is then coupled with block 80 as illustrated in FIGS. 11 and 13, it being noted that block 80 remains fixed relative to the tibia and, therefore, the resected planar tibial plateau. The alignment bridge 186 includes a dovetail slide 188 received in the slot 98 in block 80, and an arm 190 extends at an angle of 45° between slide 188 and a drill guide 192 having parallel bores 194 and 196 therethrough. Accordingly, the bores 194 and 196 will be disposed in a plane transverse to the plane of the resected tibial plateau. With the leg in full extension, as illustrated in FIGS. 11 and 13, inserts 198 and 200 are passed through bores 194 and 196, respectively, to provide elongated guides for drilling parallel bores through the femur. The bores are drilled through the femur using conventional orthopedic techniques; and, after the bores are drilled through the femur, threaded rods 204 are passed through each bore as illustrated in FIG. 14. As shown in FIG. 15, one of the threaded rods 204 is preferably hollow having a passage 206 therethrough providing communication between its end and holes 208 centrally located therein. Threaded sleeves 210 are disposed on the outer ends of each rod in threaded engagement with the rods while loosely sliding sleeves 212 are disposed between sleeves 210 and the femur, the sleeves being illustrated in FIG. 16 and shown in position relative to the femur in FIG. 14. With the sleeves tightened in place and the rods passing through the epicondylar region of the femur, a support for resecting the femoral condyle is established relative to the resected tibial plateau since the rods are disposed in a plane perpendicular to the planar tibial plateau. With the rods in place, a femoral support base 214 is rigidly attached to the rods to prevent any deflection or twisting of the rods. The femoral support base 214 includes a U-shaped member 216 having upper ends secured saddles 218 each of which has a cylindrical protrusion 220 extending upwardly therefrom and side walls 219 spaced from the cylindrical protrusion to allow the sleeves 210 to fit therebetween. Conical washers 222 are secured over the sleeves by means of screws 224 received in threaded holes 226 in the saddles 218 such that the washers abut the sleeves to firmly hold the rods in parallel position.

A femoral cutting jig 228 is mounted to the femoral support base 214 via threaded posts 230 extending through the cylindrical protrusions 220 to receive threaded nuts 232 tightening the femoral cutting jig in rigid position relative to the femoral support base. The femoral cutting jig includes a U-shaped member 234 having opposite legs pivotally mounted on flanges 236 each of which is rigidly secured to the femoral support base via threaded post 230. As best shown in FIGS. 20, 21 and 22, each of the flanges 236 has holes 238, 240 and 242 therein positioned relative to the pivotal axis indicated at 244 to position a support 246 rigidly connected with the U-shaped member 234 in a plane parallel to the plane passing through the rods through the femur as illustrated in FIG. 21, a plane perpendicular to the plane passing through the rods as illustrated in FIG. 20, and a plane positioned at an angle of 45° to the plane passing through the rods as illustrated in FIG. 22. The position of the U-shaped member and therefore the support 246 is controlled by means of spring loaded detents mounted on flanges 248 secured to the opposite ends of the U-shaped member. As shown in FIG. 23, detents 250 are biased inwardly to extend through holes 238, 240 or 242 with which they are aligned, and can be withdrawn by twisting end 252 to cause the end to cam outwardly as shown in phantom compressing a spring 254 to move the detent out of the hole. Accordingly, the femoral cutting jig can be accurately positioned in either of the three positions shown in FIGS. 20, 21 and 22 by manipulating the detents and pivoting the U-shaped member relative to the femoral support base. The femoral cutting jig illustrated in FIG. 19 differs slightly from that illustrated in FIGS. 20, 21 and 22 in that the support 246 is secured at an angle to the U-shaped member 234; however, the operation is the same in that positioning of the femoral cutting jig only requires accurate positioning of the support 246 to which the longitudinal adjustment block 66 is attached to mount the cutting platform and the cutting module in a plane perpendicular to support 246 in the same manner as described above with respect to mounting of the cutting platform and the cutting module on angular adjustment block 58 mounted on the tibial jig. FIG. 19 illustrates the milling cutter positioned at an angle of 45° to the plane of the rods 204 through the femur and further illustrates, in phantom, the milling cutter positioned in planes perpendicular and parallel to the plane of the rods 204. Since the plane of the rods 204 is parallel to the planar resected tibial plateau, the milling cutter is constrained to move only in planes parallel to a reference plane extending perpendicular to the plane of the resected tibial plateau.

To resect the femoral condyle, the stylus module 170 is mounted on the slide member 100 with the stylus 172 turned upward as illustrated at 256 in FIG. 29 and the slide member positioned in a plane parallel to the resected tibial plateau plane, and the stylus is moved to contact the lowermost point on the posterior surface of the femoral condyle. Once this point is located, the depth gauge 86 is moved to align the "zero" point with the index line on the screw 72. With the depth gauge so aligned, the stylus module is removed, and the thumbwheel 78 is rotated to move the cutting platform 7 millimeters toward the femoral condyle as indicated by the gauge 86. With the depth of cut now set and the lateral position set by viewing the position of the stylus via the arthroscope, the cutting module is positioned on the slide member and the posterior portion of the femoral condyle is resected in the same manner as described above with respect to the tibial plateau, that is, by forming a plurality of longitudinal troughs in the bone and removing the ridges therebetween by sweeping the milling cutter. With reference to FIG. 20, it can be seen that resecting of the posterior surface of the femoral condyle is accomplished by passing the milling cutter and the stylus through the same portal 168 utilized to resect the tibial plateau.

After resection of the posterior surface of the femoral condyle, the distal surface of the femoral condyle is resected by moving the femoral cutting jig to position the platform in a plane perpendicular to the plane of the rods passing through the femur and the plane of the resected posterior surface of the femoral condyle. The stylus module and the depth gauge are used in the same manner as described with respect to the resecting of the posterior surface; however, as illustrated in FIG. 21, a second portal 258 disposed between an inch and an inch and a half above portal 168 is utilized for the distal surface cutting procedure. As shown in FIG. 29, the stylus is turned toward the condyle as indicated at 260; and, when the resecting procedure is completed, the resected planar distal surface will be perpendicular to the resected planar posterior surface. Resection of the distal surface is accomplished in the same manner as described above with respect to the tibial plateau and the posterior surface.

Once resection of the distal surface is completed, the femoral cutting jig is pivoted to the position illustrated in FIG. 22 such that the platform is disposed in a plane at an angle of 45° to the distal and posterior resected surfaces. The stylus is mounted on the platform and passed through portal 258 to contact the uncut portion of the femoral condyle between the resected posterior and distal surfaces as shown at 262, and the depth gauge and cutter module are utilized in the same manner as described above to cut a chamfer surface between the distal and posterior surfaces, the chamfer surface being disposed in a plane at an angle of 45° to the planes of the distal and posterior surfaces. A plurality of semi-circular gauges 264, each having an anterior foot 266 and a posterior foot 268, are provided; and, to determine the length of the chamfer cut, individual gauges are attached to a rod 270 inserted through portal 258 and aligned with the chamfer cut to determine the size of the femoral prosthesis for use with the contoured femoral condyle.

Figure 24:
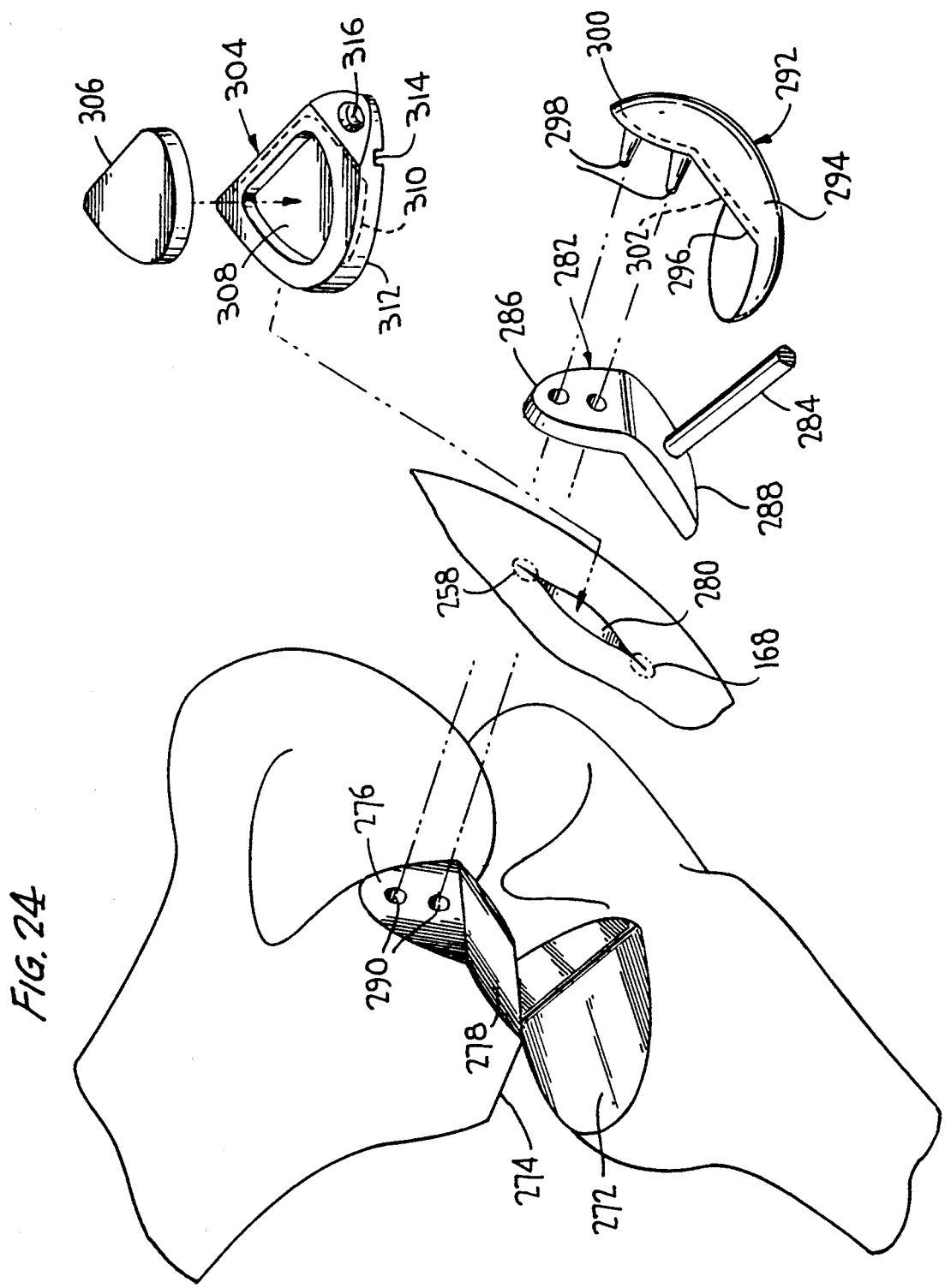
FIG. 24 is an exploded view illustrating the prepared tibial plateau and femoral condyle surfaces and positioning of the tibial and femoral prothesis components thereon.

FIG. 24 illustrates the medial compartment of the knee after resection, and it will be appreciated that the planes of each of the posterior, distal and chamfer cuts on the femoral condyle are parallel to a reference plane perpendicular to the plane of the tibial plateau, the reference plane being substantially vertical thereby producing a normal healthy knee joint. The resected planar tibial plateau is indicated at 272, the posterior planar femoral condyle cut is indicated at 274, the distal planar femoral condyle cut is indicated at 276 and the chamfer planar femoral condyle cut is indicated at 278. Once all of the resections have been performed as described above, the area between portals 168 and 258 is incised to increase the size of the portal to about one and one-half inches as indicated at 280. The tibial jig is removed once the rods are inserted in the femur to establish the femoral support base; and, once the resections are completed, the femoral support base and the femoral cutting jig are removed. A drill guide 282 mounted on a rod 284 is inserted into the joint through portal 280, the drill guide having a distal portion for abutting distal planar surface 276 and a chamfer portion 286 for abutting chamfer surface 278, the angle between portions 286 and 288 being 45° to equal the angle between distal surface 276 and chamfer surface 278. With the guide 282 aligned on the prepared femoral condyle, spaced holes 290 are drilled in the distal surface. Since the same amount of bone has been removed from each cut during contouring of the femoral condyle, a femoral prosthesis component 292 can be implanted on the femoral condyle reproducing the natural condyle. Tibial component 292 has a polycentric bearing surface 294 with an inner fixation surface 296 for engaging the posterior, distal and chamfer surfaces, and spaced tapered posts 298 extend from a distal portion of the femoral component to be received in holes 290. A channel 300 is formed in the femoral component to communicate with a recess 302 formed in the fixation surface 296 such that the femoral component can be installed in proper position on the prepared femoral condyle with the posts 298 received in the holes 290; and, thereafter, cement can be introduced between the femoral component and the bone via channel 300, the cement filling the recess 302 and producing a mechanical bond with the bone. The mechanical bond of the cement with the bone is enhanced by applying suction to rod 204, the suction being communicated via passage 206 and holes 208 and through the porous bone to draw the cement into the bone.

Prior to installation of the final tibial prothesis component, a trial tray similar in shape to tibial component 304 illustrated in FIG. 24 is placed on tibial plateau 272 via portal 280 to obtain the correct size, and various bearing inserts similar to bearing insert 306 illustrated in FIG. 24 are positioned in cavities in the tray to provide the desired tibial component thickness allowing alignment of the femur and tibia with the femoral component bearing on the bearing insert. When the proper spacing is determined, a permanent tibial prothesis implant 304 is passed through portal 280 and secured to tibial plateau 272. The tibial component 304 has a cavity 308 in the upper surface thereof for receiving bearing insert 306 in locking engagement, and, similar to femoral component 292, a recess 310 is formed in a bottom fixation surface 312 and a channel 314 communicates therewith for supplying cement to the tibial component after the tibial component is placed on the tibial plateau. A bone screw passes through an angled hole 316 in an anterior portion of the tibial prothesis 304 to hold the prothesis on the tibial plateau. The tibial and femoral prosthesis components and the bearing insert are disclosed in an application filed concurrently herewith by the same inventors entitled "Knee Joint Prosthesis", the disclosure of which is incorporated herein by reference. In practice, removable trial femoral components can be placed on the femoral condyle to assist in selection of proper tibial component thickness, and either the tibial component or the femoral component can be cemented in place before the other.

From the above, it will be appreciated that the method and apparatus of the present invention permits prosthetic knee replacement utilizing arthroscopic surgical procedures. Additionally, the method and apparatus provide advantages useful in open knee surgery also in that the cuts in accordance with the present invention are different for each individual since each cut is sensed from the surface and not from a previous cut thereby restoring a natural knee action in that making the cuts with reference to bone surfaces allows replication of the previous bone structure thereby not forcing alignment and allowing the compartment to be matched with the other compartments of the knee. Additionally, by establishing the femoral jig in the femur in relation to the tibial plateau, alignment of the femoral and tibial protheses is assured with bearing contact along a line laterally through the knee joint. The platform and cutting module permit the cutting action to be performed by the surgeon with only one hand allowing his second hand to move the arthroscope or to provide better viewing in open surgery. The resecting of bone using a pivoting movement of a cutter is particularly advantageous in that, by placing the pivot point just external of the body, small portals can be used in accordance with arthroscopic techniques.

Inasmuch as the present invention is subject to many variations, modifications and changes in detail, the subject matter discussed above and shown in the accompanying drawings is intended to be illustrative only and not to be taken in a limiting sense.

What is claimed is:

1. Apparatus for resecting bone in the body of a patient comprising
   a rotatable elongate milling cutter having a body terminating at a distal end, a plurality of radially extending end cutting edges disposed on said distal end and a plurality of side cutting edges extending along said milling cutter body for resecting bone externally of said milling cutter body whereby bone chips are produced externally thereof, and an interior passage in said milling cutter body; and
   means on said milling cutter for evacuating bone chips from externally of said milling cutter body to said interior passage for evacuation from the patient's body through said passage.

2. Apparatus for resecting bone as recited in claim 1 wherein said milling cutter is hollow and said evacuating means includes at least one aperture disposed in said milling cutter body and communicating with said interior passage.

3. Apparatus for resecting bone as recited in claim 2 including a plurality of said apertures with at least one of said apertures disposed between each pair of said side cutting edges.

4. Apparatus for resecting bone as recited in claim 3 wherein said milling cutter includes a longitudinal axis, said distal end cutting edges are disposed in a plane extending transverse to said longitudinal axis of said milling cutter and said side cutting edges each extend from one of said distal end cutting edges and having a helical configuration.

5. Apparatus for resecting a bone in the body comprising
   milling cutter means;
   platform means for supporting said milling cutter means for movements therealong in a cutting plane and including means for supporting said milling cutter means for longitudinal and pivotal movements relative to said platform means in said cutting plane;
   means for mounting said platform means relative to the bone; and
   longitudinal adjustment means coupled with said platform means for moving said platform means and said cutting plane relative to said mounting means in a direction perpendicular to said cutting plane.

6. Apparatus for resecting bone as recited in claim 5 wherein said platform means includes a pivotally mounted slide member supporting said milling cutter means for sliding movement therealong.

7. Apparatus for resecting bone as recited in claim 6 wherein said platform means includes stop means for limiting pivotal movement of said slide member.

8. Apparatus for resecting bone as recited in claim 6 wherein said platform means includes a support member pivotally mounting said slide member and selectively engageable clamp means for securing said slide member at a selected angular position relative to said support member.

9. Apparatus for resecting a bone as recited in claim 8 wherein said slide member supports said milling cutter means for movement in said cutting plane, said support member is movably mounted to adjust the position of said milling cutter means in said cutting plane, and said longitudinal adjustment means is coupled with said support member.

10. Apparatus for resecting bone as recited in claim 9 wherein said platform means includes angular adjustment means coupled with said support member for adjusting the angular orientation of said cutting plane.

11. Apparatus for resecting a bone in the body comprising
    milling cutter means;
    platform means for supporting said milling cutter means for movements therealong in a cutting plane and including means for supporting said milling cutter means for longitudinal and pivotal movements relative to said platform means in said cutting plane; and
    means for mounting said platform means relative to the bone, said mounting means including a jig for attachment to the bone and adjustment means coupled with said platform means for adjusting the angular position of said platform means relative to said jig.

12. Apparatus for resecting a bone in the body comprising
    milling cutter means;
    platform means for supporting said milling cutter means for movements therealong in a cutting plane and including means for supporting said milling cutter means for longitudinal and pivotal movements relative to said platform means in said cutting plane; and
    means for mounting said platform means relative to the bone, said mounting means including a jig for attachment to the bone and adjustment means coupled with said platform means for adjusting the longitudinal position of said platform means relative to said jig.

13. Apparatus for resecting a bone in the body comprising
    milling cutter means;
    platform means for supporting said milling cutter means for movements therealong in a cutting plane and including means for supporting said milling cutter means for longitudinal and pivotal movements relative to said platform means in said cutting plane; and
    means for mounting said platform means relative to the bone, said mounting means including a jig for attachment to the bone and adjustment means coupled with said platform means for adjusting the lateral position of said platform means relative to said jig.

14. Apparatus for resecting a bone in the body comprising milling cutter means;

platform means for supporting said milling cutter means for movements therealong in a cutting plane and including means for supporting said milling cutter means for longitudinal and pivotal movements relative to said platform means in said cutting plane; and means for mounting said platform means relative to the bone, said mounting means including a jig for attachment to the bone and adjustment means coupled with said platform means for adjusting the longitudinal and lateral positions of said platform means relative to said jig.

* * * * *